(12) United States Patent
Lee et al.

(10) Patent No.: US 8,383,153 B2
(45) Date of Patent: Feb. 26, 2013

(54) POLY(AMIDOAMINE) OLIGOMER HYDROGEL FOR DRUG DELIVERY AND DRUG CARRIER USING THE SAME

(75) Inventors: Doo Sung Lee, Suwon-si (KR); Bong Sup Kim, Suwon-si (KR); Minh Khanh Nguyen, Suwon-si (KR)

(73) Assignee: Sungyunkwan University Foundation for Corporate Collaboration, Suwon-Si (KR)

( * ) Notice: Subject to any disclaimer, the term of this patent is extended or adjusted under 35 U.S.C. 154(b) by 114 days.

(21) Appl. No.: 12/938,852

(22) Filed: Nov. 3, 2010

(65) Prior Publication Data

US 2011/0217376 A1 Sep. 8, 2011

(30) Foreign Application Priority Data

Mar. 3, 2010 (KR) .................. 10-2010-0019215

(51) Int. Cl.
| | |
|---|---|
| A61K 38/19 | (2006.01) |
| A61K 38/27 | (2006.01) |
| A61K 38/18 | (2006.01) |
| A61K 31/56 | (2006.01) |
| A61K 39/395 | (2006.01) |
| A61K 39/00 | (2006.01) |
| A61K 38/22 | (2006.01) |
| A61K 38/30 | (2006.01) |
| A61K 38/21 | (2006.01) |
| A61K 31/337 | (2006.01) |
| A61K 31/196 | (2006.01) |
| A61P 35/00 | (2006.01) |
| A61P 31/12 | (2006.01) |
| A61P 31/04 | (2006.01) |
| A61P 37/06 | (2006.01) |
| A61P 29/00 | (2006.01) |

(52) U.S. Cl. .................. 424/484; 514/448; 528/380
(58) Field of Classification Search .................. 264/401
See application file for complete search history.

(56) References Cited

U.S. PATENT DOCUMENTS

| | | | |
|---|---|---|---|
| 6,103,865 A | 8/2000 | Bae et al. | |
| 7,427,394 B2 | 9/2008 | Anderson et al. | |
| 2002/0131951 A1* | 9/2002 | Langer et al. | 424/78.37 |
| 2003/0006534 A1* | 1/2003 | Taboas et al. | 264/401 |

FOREIGN PATENT DOCUMENTS

| | | |
|---|---|---|
| KR | 10-2002-0096585 A | 12/2002 |
| KR | 10-2006-0101202 A | 9/2006 |

OTHER PUBLICATIONS

Ferruti et al.,"Novel polyamidoamine-based hydrogel with an innovative molecular architecture as a Co2+−, Ni2+−, and Cu2+− sorbing material: cyclovoltammetry and extended x-ray absorption fine structure studies." Journal of Polymer Science: Part A: Polymer Chemistry, vol. 44, 2316-2327 (2006).*
Ferruti et al., "Poly(amido-amine)s: Biomedical Applications" Macromo. Rapid Commun. vol. 23, No. 5/6; 332-355 (2002).*

* cited by examiner

*Primary Examiner* — Walter Webb
(74) *Attorney, Agent, or Firm* — Sughrue Mion, PLLC

(57) ABSTRACT

Disclosed is a temperature- and pH-sensitive hydrogel composed of a poly(amidoamine) oligomer only. The hydrogel is prepared in a simple manner and is readily released from the body. Further disclosed are a method for preparing the hydrogel and a drug carrier using the hydrogel.

11 Claims, 2 Drawing Sheets

POLY(AMIDOAMINE) OLIGOMER HYDROGEL FOR DRUG DELIVERY AND DRUG CARRIER USING THE SAME

BACKGROUND OF THE INVENTION

1. Field of the Invention

The present invention relates to a temperature- and pH-sensitive oligomer hydrogel for drug delivery and a drug carrier using the same. More particularly, the present invention relates to a hydrogel composed of poly(amidoamine) (PAA) only and a drug carrier using the hydrogel.

2. Description of the Related Art

Drug carriers using polymer hydrogels have been developed. For example, U.S. Pat. No. 5,476,909 describes a biodegradable triblock (A-B-A) copolymer in the form of polyester wherein the hydrophobic blocks (A) are limited to polylactide (PLA), polyglycolide (PGA) and copolymers thereof, and the hydrophilic block (B) is limited to polyethylene glycol (PEG) and derivatives thereof.

The triblock copolymer consisting of the hydrophobic polymer and the hydrophilic polymer is sensitive to temperature and undergoes sol-gel transition in response to temperature changes. After the block copolymer in the form of an aqueous solution (i.e. a sol state) is injected into the body, it is changed to a gel state by the body temperature. This sol-gel transition enables the utilization of the block copolymer as a support of a sustained-release drug carrier that stably contains a drug and slowly releases and delivers the drug in the body. However, the sol-gel transition of the block copolymer sensitive to temperature only leads to a weak interaction with a drug, causing initial burst release of the drug after injection into the body. Further, the temperature of a syringe needle through which the block copolymer is injected into the body reaches thermal equilibrium with the body temperature. As a result, the block copolymer is gelled to clog the needle before it is completely injected into the body.

SUMMARY OF THE INVENTION

It is an object of the present invention to provide a poly(amidoamine) (PAA) oligomer hydrogel that is prepared in a relatively easy manner, is completely released from the body, and undergoes sol-gel transition depending on temperature and pH changes.

It is another object of the present invention to provide a method for preparing the PAA oligomer hydrogel.

It is another object of the present invention to provide a drug carrier using the PAA oligomer hydrogel.

It is another object of the present invention to provide a new concept of temperature- and pH-sensitive oligomer hydrogel whose molecular structure is designed to inhibit initial burst release of a drug and enable sustained release of the drug, thus being suitable for use as a drug carrier.

It is another object of the present invention to provide a method for preparing the oligomer hydrogel.

It is another object of the present invention to provide a drug carrier comprising the oligomer hydrogel and at least one physiologically active substance.

It is another object of the present invention to provide a temperature- and pH-sensitive oligomer hydrogel designed to target cancer cells and direct targets in various applications, for example, genetic variation, by optimally varying the kind, molar ratio and molecular weight of constituents of the oligomer.

It is another object of the present invention to provide a method for preparing the oligomer hydrogel.

It is still another object of the present invention to provide a drug carrier using the oligomer hydrogel.

According to an aspect of the present invention, there is provided a temperature- and pH-sensitive oligomer hydrogel composed of a poly(amidoamine) (PAA) oligomer only.

In an embodiment, the PAA oligomer is a low molecular weight polymer of Formula 1:

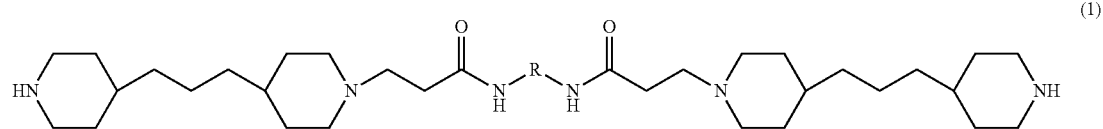

(1)

wherein R is a $C_1$-$C_{10}$ alkyl group.

In an embodiment, the PAA oligomer is prepared by coupling between at least one alkylene bisacrylamide compound and at least one diamine compound having secondary amine groups as precursors.

In an embodiment, the PAA oligomer has a molecular weight of 500 to 1,000 g/mol.

In an embodiment, the PAA oligomer forms a hydrogel at a pH of 7.0 to 7.4 and a sol at a pH of 3.0 to less than 7.0.

In an embodiment, the alkylene bisacrylamide compound is represented by Formula 2:

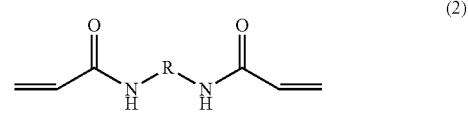

(2)

wherein R is a $C_1$-$C_{10}$ alkyl group.

In an embodiment, the alkylene bisacrylamide compound is selected from the group consisting of N,N'-methylene bisacrylamide (MDA), N,N'-ethylene bisacrylamide, N,N-diisopropylacrylamide, 1,4-butylene diacrylamide, 1,6-hexylene diacrylamide, 1,8-octylene diacrylamide, 1,10-decane diacrylamide, and mixtures thereof.

In an embodiment, the diamine compound is selected from the group consisting of secondary amine group-containing diamine compounds of Formula 3:

(3)

wherein $R_1$ and $R_2$ are each independently a $C_1$-$C_{10}$ alkyl group, and mixtures thereof.

In an embodiment, the diamine compound having secondary amine groups is selected from the group consisting of 4,4'-trimethylenepiperidine, N,N'-dimethylethylenediamine, piperazine, 2-methylpiperazine, 3-methyl-4-(3-methylphenyl)piperazine, 3-methylpiperazine, 4-(phenylmethyl)piperazine, 4-(1-phenylethyl)piperazine, 4-(1,1'-dimethoxycarbonyl)piperazine, 4-(2-(bis-(2-propenyl)amino)ethyl) piperazine, 1-(2-aminoethyl)piperazine, {4-(aminomethyl) piperazine, N,N'-dimethyl-1,2-ethanediamine, N,N'-diethyl-1,2-ethanediamine, N,N'-diisopropyl-1,2-ethanediamine, N,N'-dimethyl-1,2-propyldiamine, N,N'-diethyl-1,2-propyldiamine, N,N'-diisopropyl-1,2-propyldiamine, N,N'-dimethyl-1,2-hexanediamine, N,N'-dimethyl-N-[3-(methylamino)propyl]-1,3-propanediamine, N-[2-methylamino) ethoxyethyl]-N,N'-dimethylamine, N-[2-methylamino) dioxyethyl]-N,N'-dimethylamine, N-[2-methylamino) dioxyethyl]-N,N'-dimethylamine, 1,4-diazepane, and mixtures thereof.

In an embodiment, the PAA oligomer is prepared by the reaction of the alkylene bisacrylamide compound with the diamine compound in a molar ratio of 1:10-50.

According to another aspect of the present invention, there is provided a drug carrier comprising the PAA oligomer hydrogel.

According to yet another aspect of the present invention, there is provided a drug carrier comprising the PAA oligomer hydrogel and at least one physiologically active substance.

In an embodiment, the physiologically active substance is selected from the group consisting of: proteins, including insulin, granulocyte-colony stimulating factor (G-CSF), human growth hormone (hGH), erythropoietin (EPO), symlin, exendin and somatokine; anticancer agents, including paclitaxel, docetaxel, chlorambucil, interferon, monoclonal antibodies and vaccines; antibacterial agents; steroids; anti-inflammatory agents; sex hormones; immunosuppressants; antiviral agents; anesthetics; antiemetics; and antihistaminic agents.

In an embodiment, the drug carrier may further comprise at least one additive selected from the group consisting of excipients, stabilizers, pH-adjusting agents, antioxidants, preservatives, binders and disintegrants, and/or at least one solvent.

In an embodiment, the drug carrier is administered orally or parenterally. In a preferred embodiment, the drug carrier is in the form of a preparation for intravenous, intramuscular or subcutaneous injection.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
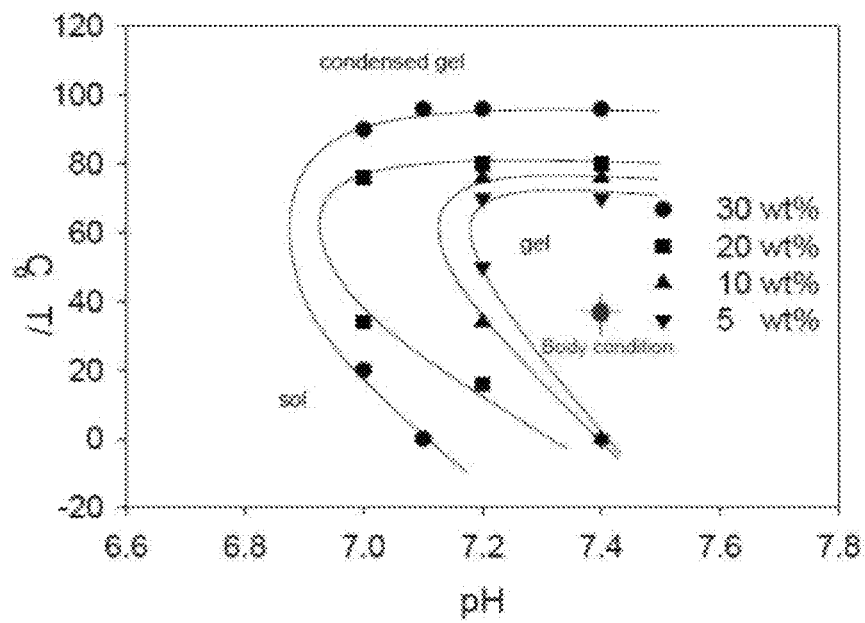
FIG. 1 is a graph showing the sol-gel transition behavior of a PAA oligomer prepared in Example 7 at various concentrations with varying temperatures and pH values.

Preferred embodiments of the present invention will now be described in detail with reference to the accompanying drawings. It should be noted that whenever possible, the same reference numerals will be used throughout the drawings and the description to refer to the same or like parts. In describing the present invention, detailed descriptions of related known functions or configurations are omitted in order to avoid making the essential subject of the invention unclear.

As used herein, the terms "about", "relatively", etc. are intended to allow some leeway in mathematical exactness to account for tolerances that are acceptable in the trade and to prevent any unconscientious violator from unduly taking advantage of the disclosure in which exact or absolute numerical values are given so as to help understand the invention.

When the conventional temperature-sensitive block copolymer hydrogel, which is composed of a polyethylene glycol compound and a biodegradable polymer selected from polylactide, polyglycolide, polycaprolactone and copolymers thereof, is accumulated in the body or is released from the body after being injected into the body, biodegradation by-products may cause side effects described above.

For the purpose of solving the problems of the prior art, the present inventors have prepared an oligomer hydrogel composed of a PAA oligomer only that exhibits hydrophilicity or hydrophobicity depending on the ionization degree in response to pH changes without the use of any hydrophobic aliphatic polyester or temperature-sensitive hydrophilic polyethylene glycol compound.

The present inventors have found that the oligomer hydrogel can be prepared in a relatively simple manner, is completely released from the body due to its low molecular weight, and is sensitive to temperature and pH. The present inventors have also found that the PAA oligomer hydrogel is gelled at a pH of 7.0 to 7.4 similar to the body condition and is changed to a sol at a pH lower than 7.0 ("sol-gel transition") to prevent initial burst release of a drug and clogging of an injection needle, which are problems of the conventional temperature-sensitive hydrogel, and a gel can be formed safely in the body after the PAA oligomer hydrogel is injected into the body, thus being suitable for use as a drug carrier capable of directing targets and sustained-release at particular temperature and pH.

Thus, the present invention provides a temperature- and pH-sensitive oligomer hydrogel composed of a poly(amidoamine) (PAA) oligomer only.

The PAA oligomer preferably has a number average molecular weight (Mn) in the range of 500 to 1,000. If the number average molecular weight of the PAA oligomer is out of the range defined above (i.e. lower than 500 or higher than 1,000), sol-gel transition of the oligomer hydrogel is not likely to occur. Even when a gel is formed, the gel is insufficient in strength and shows polymer hydrogel characteristics, which are contrary to the objects that the present invention intends to attain and make it practically difficult to use as a drug carrier.

The PAA oligomer hydrogel of the present invention is prepared in a relatively simple manner by a one-step process, for example, as depicted in the following reaction.

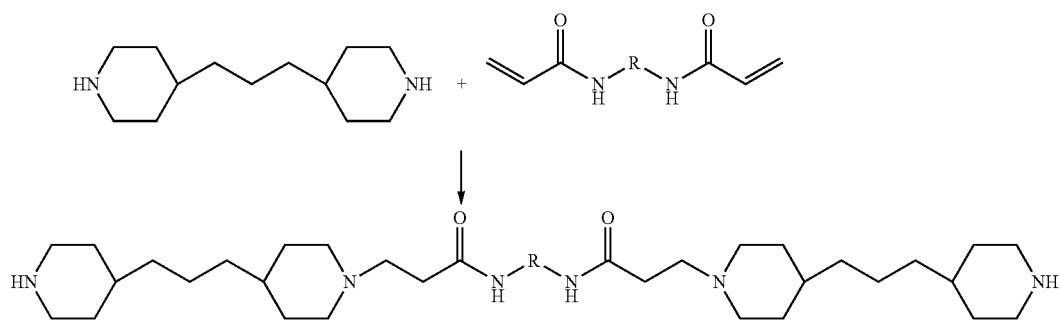

wherein R is a $C_1$-$C_{10}$ alkyl group.

Specifically, the PAA oligomer hydrogel of the present invention is prepared by coupling between secondary amine groups (—NH) of a diamine compound and vinyl groups ($CH_2$=CH—) of an alkylene bisacrylamide compound as precursors.

There is no particular restriction on the reaction conditions (e.g., temperature and time) for the preparation of the PAA oligomer hydrogel.

The alkylene bisacrylamide compound is selected from the group consisting of N,N'-methylene bisacrylamide (MDA), N,N'-ethylene bisacrylamide, N,N-diisopropylacrylamide, 1,4-butylene diacrylamide, 1,6-hexylene diacrylamide, 1,8-octylene diacrylamide, 1,10-decane diacrylamide, and mixtures thereof.

The diamine compound having secondary amine groups is selected from the group consisting of 4,4'-trimethylenepiperidine, N,N'-dimethylethylenediamine, piperazine, 2-methylpiperazine, 3-methyl-4-(3-methylphenyl)piperazine, 3-methylpiperazine, 4-(phenylmethyl)piperazine, 4-(1-phenylethyl)piperazine, 4-(1,1'-dimethoxycarbonyl)piperazine, 4-(2-(bis-(2-propenyl)amino)ethyl)piperazine, 1-(2-aminoethyl)piperazine, {4-(aminomethyl)piperazine, N,N'-dimethyl-1,2-ethanediamine, N,N'-diethyl-1,2-ethanediamine, N,N'-diisopropyl-1,2-ethanediamine, N,N'-dimethyl-1,2-propyldiamine, N,N'-diethyl-1,2-propyldiamine, N,N'-diisopropyl-1,2-propyldiamine, N,N'-dimethyl-1,2-hexanediamine, N,N'-dimethyl-N-[3-(methylamino)propyl]-1,3-propanediamine, N-[2-methylamino)ethoxyethyl]-N,N'-dimethylamine, N-[2-methylamino)dioxyethyl]-N,N'-dimethylamine, N-[2-methylamino)dioxyethyl]-N,N'-dimethylamine, 1,4-diazepane, and mixtures thereof.

The introduction of the respective functional groups and the reactions between the end groups of the precursors were confirmed by FT-IR and $^1$H-NMR. Gel permeation chromatography (GPC) was used to determine the increased molecular weight of the PAA oligomer, confirming that the PAA oligomer is a coupling product of the precursors. The sol-gel transition of the PAA oligomer hydrogel was observed with varying pH values and temperatures to confirm the pH sensitivity of the PAA oligomer hydrogel. As a result of the observations, it was found that the PAA oligomer possesses pH sensitivity (see FIG. 1).

The present invention also provides a drug carrier comprising (a) the temperature- and pH-sensitive PAA oligomer hydrogel, and (b) at least one physiologically active substance included in the PAA oligomer hydrogel.

Non-limiting examples of the physiologically active substance include: proteins, such as insulin, granulocyte-colony stimulating factor (G-CSF), human growth hormone (hGH), erythropoietin (EPO), symlin, exendin and somatokine; anti-cancer agents, such as paclitaxel, docetaxel, chlorambucil, interferon, monoclonal antibodies and vaccines; antibacterial agents; steroids; anti-inflammatory agents; sex hormones; immunosuppressants; antiviral agents; anesthetics; antiemetics; and antihistaminic agents. In addition to these physiologically active substances, the drug carrier may further comprise at least one additive selected from the group consisting of excipients, stabilizers, pH-adjusting agents, antioxidants, preservatives, binders and disintegrants, and/or at least one solvent. The additive and the solvent may be those well known in the art.

The drug carrier may be formulated into a preparation for oral or parenteral administration, for example, intravenous, intramuscular or subcutaneous injection.

The present invention also provides a method of using the temperature- and pH-sensitive PAA oligomer hydrogel as a carrier for drug delivery. Any substance known to be effective in treating, preventing or diagnosing diseases may be included in the PAA oligomer hydrogel without particular limitation.

The present invention will be explained with reference to the following examples.

EXAMPLES

Examples 1 to 9

Synthesis of Poly(Amidoamine) (PAA) Oligomers)

Example 1

Preparation of PAA Oligomer 1,10-Decylene diacrylamide (DDA) was dissolved in a solution of 30 g of 4,4'-trimethylenedipiperidine (TMDP) in 100 ml of methanol at room temperature. The solution was allowed to react at 50° C. for 24 hr. After completion of the reaction, the reaction solution was precipitated three times by mixing with excess acetone and chloroform as a non-solvent to remove unreacted reactants. The precipitate was dried in a vacuum dryer at 40° C. for 48 hr, affording a PAA oligomer (yield≧70%) having a number average molecular weight of 500 g/mol.

Example 2

The procedure of Example 1 was repeated to prepare a PAA oligomer (yield≧70%) having a number average molecular weight of 650 g/mol.

Example 3

The procedure of Example 1 was repeated to prepare a PAA oligomer (yield≧70%) having a number average molecular weight of 850 g/mol.

Example 4

The procedure of Example 1 was repeated to prepare a PAA oligomer (yield≧70%) having a number average molecular weight of 1,000 g/mol.

Example 5

A PAA oligomer (yield≧70%) having a molecular weight of 500 g/mol was prepared in the same manner as in Example 1, except that piperazine was used as a diamine compound.

Example 6

A PAA oligomer (yield≧70%) having a molecular weight of 700 g/mol was prepared in the same manner as in Example 1, except that piperazine was used as a diamine compound.

Example 7

A PAA oligomer (yield≧70%) having a molecular weight of 900 g/mol was prepared in the same manner as in Example 1, except that 1,8-octylene diacrylamide (ODA) was used as an alkylene bisacrylamide compound.

Example 8

A PAA oligomer (yield≧70%) having a molecular weight of 900 g/mol was prepared in the same manner as in Example 1, except that 1,6-hexylene diacrylamide (HDA) was used as an alkylene bisacrylamide compound.

Example 9

A PAA oligomer (yield≧70%) having a molecular weight of 900 g/mol was prepared in the same manner as in Example 1, except that methylene diacrylamide (HDA) was used as an alkylene bisacrylamide compound.

Comparative Example 1

The procedure of Example 1 was repeated to prepare a PAA oligomer (yield=45%) having a number average molecular weight of 400 g/mol.

Comparative Example 2

The procedure of Example 1 was repeated to prepare a PAA oligomer (yield=50%) having a number average molecular weight of 1,200 g/mol.

Experimental Example 1

Evaluation of Sol-Gel Transition Behavior in Response to pH Changes

The sol-gel transition behaviors of the PAA oligomers prepared in Examples 1-9 were evaluated with varying temperatures and pH values.

First, 10% by weight of each of the PAA oligomers prepared in Examples 1-8 was dissolved in a buffer solution and titrated with a NaOH solution at 50° C. to prepare solutions having pH values of 5.5, 6.0, 6.5, 7.0 and 7.5. Then, the resulting solutions were heated by 2° C. and were allowed to stand for 10 min to reach equilibrium at a constant temperature. The reactors were tilted to evaluate the sol-gel transition behaviors of the PAA oligomer. FIG. 1 shows the sol-gel transition behaviors of the PAA oligomer prepared in Example 7 with varying temperatures and pH values.

Figure 2:
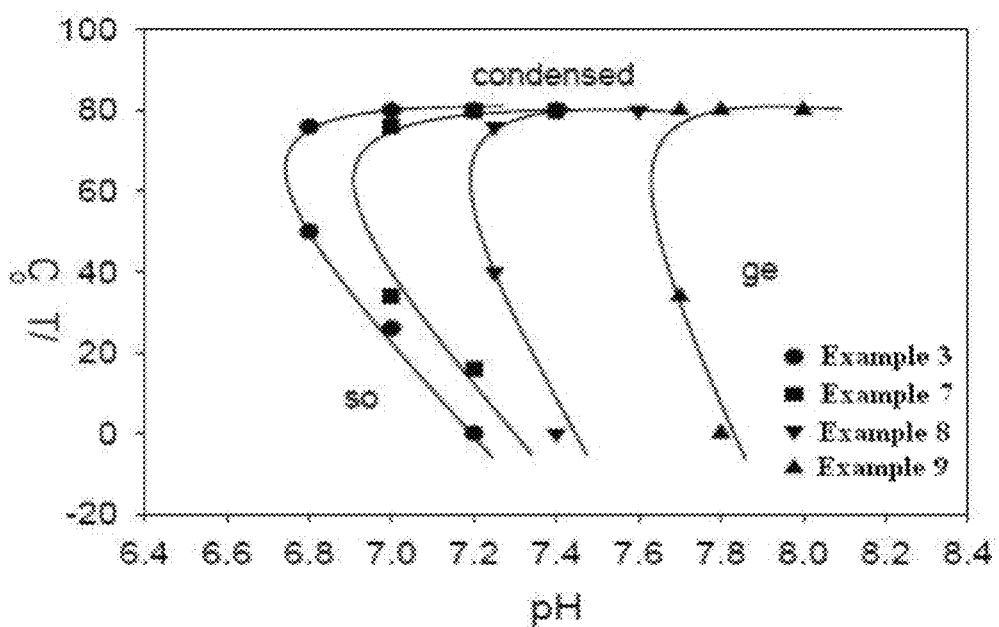
FIG. 2 is a graph showing the sol-gel transition behaviors of PAA oligomers prepared in Examples 3, 7, 8 and 9 with varying temperatures and pH values.

FIGS. 1 and 2 reveal that the ionization degree and hydrophobicity of the block PAA oligomers were varied in response to the pH changes, leading to reversible sol-gel transition behaviors of the block PAA oligomers with varying temperatures and pH values.

Experimental Example 2

Evaluation of Gel Strength

To evaluate the gel strength of the PAA oligomers prepared in Examples 1-9 after sol-gel transition with varying temperature and pH changes, the viscosity values of the PAA oligomers were measured at different temperatures by the following procedure.

First, 30% by weight of each of the PAA oligomers was dissolved in a buffer solution and titrated with a NaOH solution at 50° C. to adjust the pH to 7.4. As a result, the PAA oligomer was completely gelled to form a hydrogel. The hydrogel was allowed to stand to reach equilibrium. Thereafter, the viscosity of the hydrogel was measured using a gel rheometer. Specifically, the hydrogel sample was placed between two parallel plates of the gel rheometer in an oscillation mode under the following conditions. Controlled stress=0.4 Pa, frequency=1 rad/s, gap=0.25 mm; heating rate=1° C./min.

Figure 3:
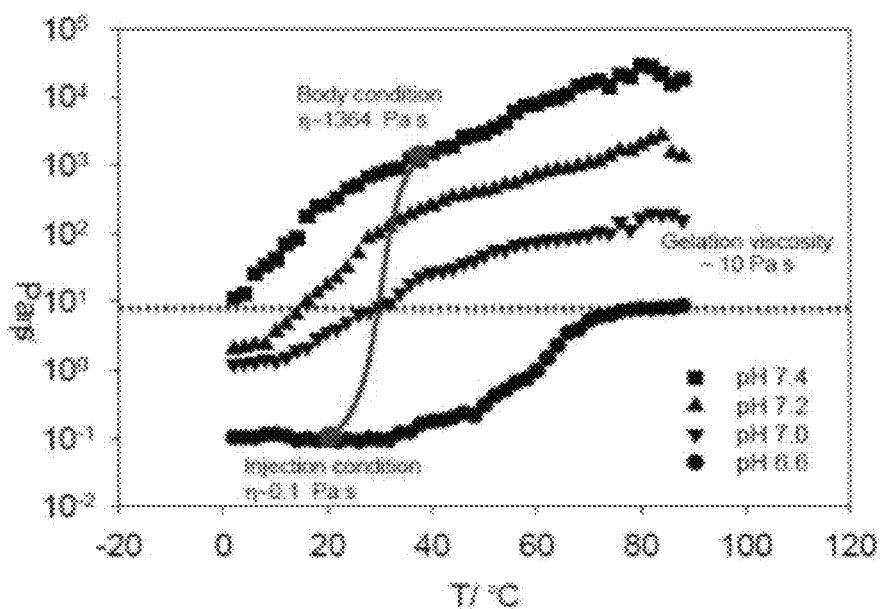
FIG. 3 is a graph showing changes in the viscosity of a PAA oligomer prepared in Example 7 at various pH values with increasing temperature.
Figure 4:
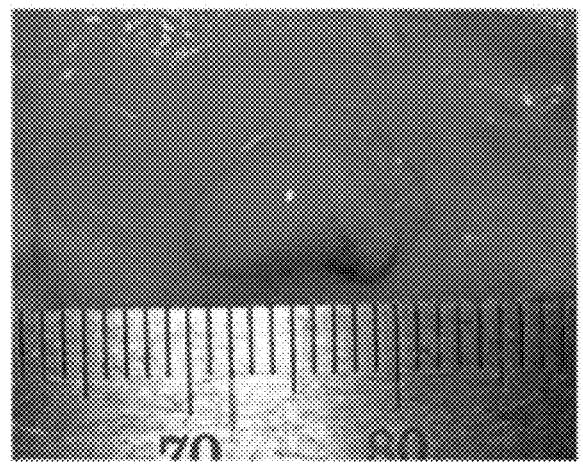
FIG. 4 is a photograph showing a gel formed 5 minutes after a 20% injectable solution of a PAA oligomer prepared in Example 7 in PBS was injected into a mouse as an animal model.

FIG. 3 is a graph showing changes in the viscosity of the PAA oligomer prepared in Example 7 at various pH values with varying temperatures.

As is apparent from the foregoing, the PAA oligomer hydrogel of the present invention is prepared in a relatively simple manner by a one-step process and is fast released from the body without being accumulated in the body due to the low molecular weight (≦1,000) of the PAA oligomer. The precursors for the preparation of the PAA oligomer by coupling exhibit hydrophilicity or hydrophobicity due to the pH-dependent ionization of the secondary amine groups so that the PAA oligomer hydrogel can be imparted with sensitivity to both temperature and pH. Therefore, the problems of conventional temperature-sensitive polymer hydrogels can be solved.

In addition, the PAA oligomer forms a stable hydrogel at a pH of 7.0 to 7.4, which corresponds to the pH range of normal body cells, and forms a sol in the pH range of 3.0 to less than 7.0, which is the pH range of abnormal cells, such as cancer cells, making it possible to use as a carrier for drug release to target cancer cells. In other words, a pH lower than 7.0 increases the ionization degree of the secondary amine groups present in the poly(amidoamine) (PAA) oligomer, rendering the PAA oligomer water-soluble (i.e. a sol) as a whole, whereas a pH of 7.0 or higher decreases the ionization degree of the PAA oligomer, rendering the PAA oligomer hydrophobic (i.e. a gel). Based on this pH-dependence, the PAA oligomer hydrogel of the present invention can exhibit sol-gel transition sensitive to pH as well as temperature.

Furthermore, the PAA oligomer hydrogel of the present invention can be used in various applications, including medical, gene delivery, drug delivery, particularly sustained-release drug carriers, due to its safety in the body. The PAA oligomer hydrogel of the present invention can be used in diagnostic applications, such as diagnostic imaging, because of its ability to deliver a substance for disease diagnosis to abnormal cells.

Moreover, the PAA oligomer hydrogel of the present invention is designed to be useful in targeting cancer cells because it form a stable hydrogel at a pH of 7.0 to 7.4, which is the same normal body condition, and to form a sol at a pH lower than 7.0, which is the pH of abnormal cells, such as cancer cells. Further, the PAA oligomer hydrogel of the present invention is further designed to target cancer cells and direct targets in various applications, for example, genetic variation, by appropriately varying the kind, molar ratio and molecular weight of constituents of the oligomer hydrogel and/or the functional groups of the blocks.

Although the present invention has been described herein with reference to the foregoing embodiments and accompanying drawings, the scope of the present invention is not limited to the embodiments. Therefore, it will be evident to those skilled in the art that various substitutions, modifications and changes are possible, without departing from the spirit of the invention as disclosed in the accompanying claims.

What is claimed is:

1. A temperature- and pH-sensitive oligomer hydrogel for drug delivery wherein the hydrogel is composed of a poly (amidoamine) (PAA) oligomer only,
wherein the PAA oligomer is represented by Formula 1:

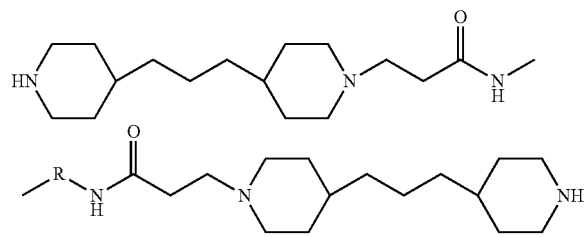

wherein R is a $C_1$-$C_{10}$ alkyl group.

2. The hydrogel of claim 1, wherein the PAA oligomer has a number average molecular weight (Mn) of 500 to 1,000.

3. The hydrogel of claim 1, wherein the PAA oligomer is prepared by coupling between at least one alkylene bisacrylamide compound and at least one diamine compound having secondary amine groups as precursors.

4. The hydrogel of claim 3, wherein the alkylene bisacrylamide compound is selected from the group consisting of N,N'-methylene bisacrylamide (MDA), N,N'-ethylene bisacrylamide, N,N-diisopropylacrylamide, 1,4-butylene diacrylamide, 1,6-hexylene diacrylamide, 1,8-octylene diacrylamide, 1,10-decane diacrylamide, and mixtures thereof.

5. The hydrogel of claim 3, wherein the diamine compound having secondary amine groups is selected from the group consisting of 4,4'-trimethylenepiperidine, N,N'-dimethylethylenediamine, piperazine, 2-methylpiperazine, 3-methyl-4-(3-methylphenyl)piperazine, 3-methylpiperazine, 4-(phenylmethyl)piperazine, 4-(1-phenylethyl)piperazine, 4-(1,1'-dimethoxycarbonyl)piperazine, 4-(2-(bis-(2-propenyl)amino)ethyl)piperazine, 1-(2-aminoethyl)piperazine, {4-(aminomethyl)piperazine, N,N'-dimethyl-1,2-ethanediamine, N,N'-diethyl-1,2-ethanediamine, N,N'-diisopropyl-1,2-ethanediamine, N,N'-dimethyl-1,2-propyldiamine, N,N'-diethyl-1,2-propyldiamine, N,N'-diisopropyl-1,2-propyldiamine, N,N'-dimethyl-1,2-hexanediamine, N,N'-dimethyl-N-[3-(methylamino)propyl]-1,3-propanediamine, N-[2-methylamino)ethoxyethyl]-N,N'-dimethylamine, N-[2-methylamino)dioxyethyl]-N,N'-dimethylamine, N-[2-methylamino)dioxyethyl]-N,N'-dimethylamine, 1,4-diazepane, and mixtures thereof.

6. The hydrogel of claim 3, wherein the alkylene bisacrylamide compound is reacted with the diamine compound in a molar ratio of 1:10-50.

7. The hydrogel of claim 3, wherein the PAA oligomer forms a hydrogel at a pH of 7.0 to 7.4 and a sol at a pH of 3.0 to less than 7.0.

8. A drug carrier comprising the hydrogel of any of claims 1 to 7.

9. A drug carrier comprising the hydrogel of any of claims 1 to 7 and at least one physiologically active substance included in the hydrogel.

10. The drug carrier of claim 9, wherein the physiologically active substance is selected from the group consisting of: proteins, insulin, granulocyte-colony stimulating factor (G-CSF), human growth hormone (hGH), erythropoietin (EPO), symlin, exendin and somatokine; anticancer agents, paclitaxel, docetaxel, chlorambucil, interferon, monoclonal antibodies and vaccines; antibacterial agents; steroids; anti-inflammatory agents; sex hormones; immunosuppressants; antiviral agents; anesthetics; antiemetics; and antihistaminic agents, and the drug carrier further comprises at least one additive selected from the group consisting of excipients, stabilizers, pH-adjusting agents, antioxidants, preservatives, binders and disintegrants, and/or at least one solvent.

11. The drug carrier of claim 9, wherein the drug carrier is administered orally or parenterally in the form of a preparation for intravenous, intramuscular or subcutaneous injection.

* * * * *

UNITED STATES PATENT AND TRADEMARK OFFICE
CERTIFICATE OF CORRECTION

PATENT NO. : 8,383,153 B2
APPLICATION NO. : 12/938852
DATED : February 26, 2013
INVENTOR(S) : Doo Sung Lee et al.

It is certified that error appears in the above-identified patent and that said Letters Patent is hereby corrected as shown below:

Title Page: Item (73) Assignee: delete "Sungyunkwan University Foundation for Corporate Collaboration" and insert -- Sungkyunkwan University Foundation for Corporate Collaboration --

Signed and Sealed this
Twenty-sixth Day of November, 2013

Margaret A. Focarino
*Commissioner for Patents of the United States Patent and Trademark Office*